United States Patent [19]

Fenner

[11] Patent Number: 5,561,699

[45] Date of Patent: Oct. 1, 1996

[54] OPERATING MECHANISM FOR X-RAY SYSTEM

[75] Inventor: Knut T. Fenner, New York, N.Y.

[73] Assignee: Siemens Aktiengesellschaft, Munich, Germany

[21] Appl. No.: 435,429

[22] Filed: May 10, 1995

[30] Foreign Application Priority Data

Jun. 22, 1994 [DE] Germany .......................... 44 21 798.6

[51] Int. Cl.⁶ ................................................ H05G 1/00
[52] U.S. Cl. ............................................. 378/208; 378/204
[58] Field of Search .................................. 378/209, 208, 378/204, 197

[56] References Cited

U.S. PATENT DOCUMENTS

| | | | |
|---|---|---|---|
| 4,127,775 | 11/1978 | Ohlson | 378/197 |
| 4,926,456 | 5/1990 | Bock et al. | 378/209 |
| 5,400,792 | 3/1995 | Hoebel et al. | |

FOREIGN PATENT DOCUMENTS 9218103  8/1993  Germany .
4218019  9/1993  Germany .

*Primary Examiner*—Craig E. Church
*Attorney, Agent, or Firm*—Hill, Steadman & Simpson

[57] ABSTRACT

An operating mechanism for an X-ray system has a carrier for a number of operating elements which is connected to the patient table so as to be pivotable around an axis extending parallel to the longitudinal axis of the patient table. The carrier has two generally U-shaped sides, with one leg of each U-shaped sides being connected to the patient support table in a pivotable manner, and the other leg of each U-shaped side being connected to a generally longitudinally extending connector section. The operating elements are removably mounted on the connector section. The carrier is connected at one side of the patient support table, and feed and control lines for the operating elements can be conducted inside the carrier to the operating elements. The carrier may have a touch-sensitive patch strip embedded therein so that, when the carrier is gripped by an attendant, a control element for assisting in the positional adjustment of the patient support table is activated. The operating mechanism provides patient-proximate, simple operation of all components of the x-ray system by one or more persons.

9 Claims, 2 Drawing Sheets

1
OPERATING MECHANISM FOR X-RAY SYSTEM

BACKGROUND OF THE INVENTION

1. Field of the Invention

The present invention is directed to an operating mechanism for a medical examination apparatus, and in particular to an operating mechanism for an x-ray system.

2. Description of the Prior Art

Various operating mechanisms are known for operating x-ray systems. Such operating mechanisms include control panels having keys and levers, joysticks, and similar operating elements. In complicated x-ray systems having a large number of components which must be operated, it is common to centralize the operation of all components proceeding from a central control panel.

SUMMARY OF THE INVENTION

It is an object of the present invention to provide an operating mechanism for an x-ray system which permits one or more persons to undertake operation of the x-ray system in the examination room proceeding from a location proximate to the examination table.

It is a further object of the present invention to provide such an x-ray system which permits control of the x-ray system in a "user friendly" and reliable manner, both for the operating personnel and the patient, without impeding free access to the patient.

The above objects are achieved in accordance with the principles of the present invention in an operating mechanism for an x-ray system having a carrier for a number of control elements which is pivotably mounted at one side of the patient support table. (Another identical carrier with duplicate operating elements can be mounted at the other side of the patient support table, if desired.) The carrier is a continuous element, such as a tubular element, having opposite U-shaped sides. One leg of each U-shaped side is pivotably connected to the support table, and the other leg of each U-shaped side is connected to a connector which joins the sides. The connector is substantially straight and extends substantially parallel to the longitudinal axis of the patient support table. The operating elements are removably mounted on this straight connector. By means of the pivotable connection, the carrier and the operating elements thereon can be pivoted from a standby position, which is beneath the support surface of the table and thus does not impede patient placement on, or patient removal from, the support surface, to a position wherein the operating elements are supported in a cantilevered fashion at the side of the support table for use by operating personnel. Operation in a "user friendly" manner is thereby achieved, while simultaneously provided for removability, replacement, displacement, and rotation of the operating elements as needed.

If the carrier is in the form of a tube, connecting lines for supplying power to the operating elements can be contained within the carrier, with electrical contact being made to each of the operating elements by a releasable connection. The operating elements are preferably remote control elements, and therefore the only lines leading thereto through the carrier are those needed for power supply; the control signals which are sent from and received by the operating elements are preferably transmitted wirelessly.

2

The carrier can also be provided with a touch-sensitive patch strip which is connected in a circuit which includes a position control elements, such as a magnetic break, for the support surface of the table. Merely gripping the carrier, which is shaped so as to facilitate manual moving of the support surface via the carrier, thereby releases the magnetic break, permitting adjustment of the support surface.

DESCRIPTION OF THE PREFERRED EMBODIMENTS

Figure 1:
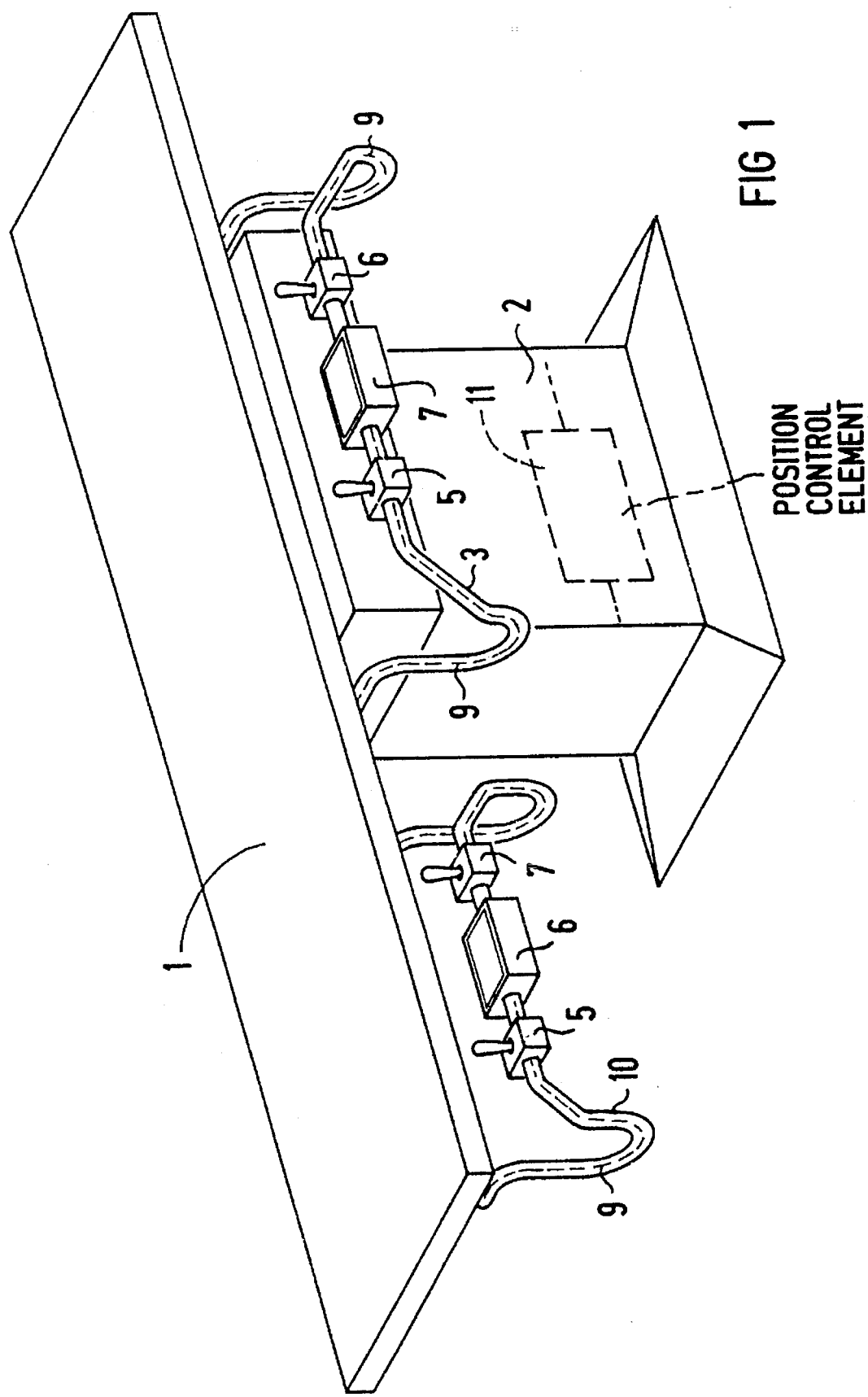
FIG. 1 is a perspective view of a patient support table having an operating mechanism constructed in accordance with the principles of the present invention, for a medical examination apparatus such as an x-ray system.

The patient support table and operating mechanism shown in FIG. 1 are for use with a medical examination apparatus, such as an x-ray system, of a known type. Such known systems have a number of components which have variable or settable operating parameters and/or which must be relatively adjusted in position. Such components include, for example, the x-ray tube and its high-voltage supply, the x-ray detector, such as an x-ray image intensifier, various components of the video processing chain, and the patient support table itself.

The patient support table shown in FIG. 1 has a support surface 1 and a base or pedestal 2 which may be a part of an x-ray system for conducting, for example, angiographic examinations.

Figure 2:
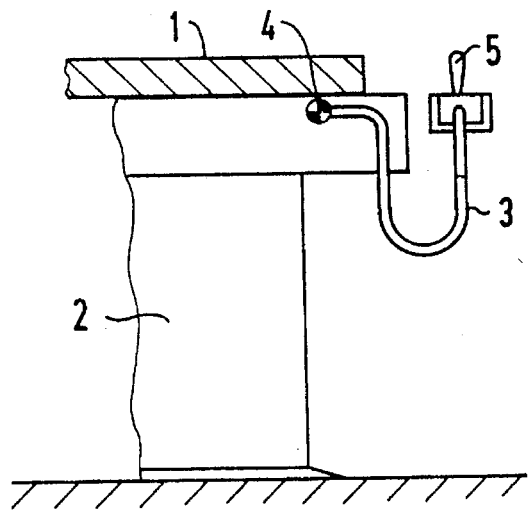
FIGS. 2 and 3 respectively show side elevational views of a portion of the support table and operating mechanism shown in FIG. 1, with the operating mechanism in two different positions.
Figure 3:
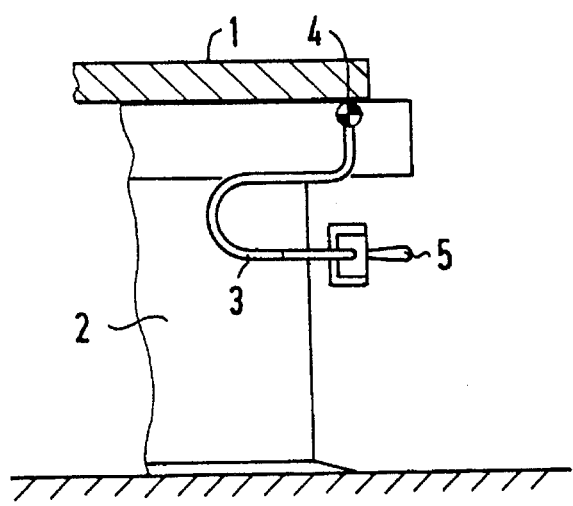

An operating mechanism in accordance with the principles of the present invention is formed by a carrier 3 which is mounted at a long side of the support surface 1. The carrier 3 is connected to the patient support table so as to be pivotable around an axis which extends parallel to the longitudinal axis of the patient support table. The pivotable connection and axis are indicated at 4 in FIGS. 2 and 3. The carrier 3 has U-shaped sides at opposite ends thereof, with each U-shaped side having one leg connected to the pivotable connection 4, and another leg connected to a generally straight section, which connects the two sides of the carrier 3. The leg of each U-shaped side connected to the straight section may be angled inwardly toward a center of the carrier 3. The straight section extends substantially parallel to the aforementioned longitudinal axis.

A plurality of operating elements are removably mounted on the straight section of the carrier 3. In the exemplary embodiment shown in FIG. 1, these operating elements include two joysticks 5 and 6 and a touch-control pad (mouse pad) 7. The operating elements 5, 6 and 7 individually or in combination control the aforementioned components of the x-ray system.

The carrier 3 is secured to the patient support table beneath the support surface 1, and has defined latched or detent positions when rotated. The position of the carrier 3 shown in FIG. 2 allows easy operation by an attendant, because the operating elements 5, 6 and 7 project outwardly and are held in a cantilevered manner by the carrier 3 so as to be easily manipulated. The position of the carrier 3 beneath the support surface 1 shown in FIG. 3 enables easy access to the support surface 1 for unimpeded placement and removal of the patient to and from the support surface 1. Further intermediate latched or detent positions enable the position of the carrier 3 to be adapted to users of differing physical size. Unimpeded access to a patient on the support surface 1 is also provided when the carrier 3 is in the position shown in FIG. 3.

The operating elements 5, 6 and 7 are removably held on the carrier 3, for example, by releasable clamps. The operating elements 5, 6 and 7 are preferably wireless remote control elements, with communication between the operating elements 5, 6 and 7 and the components operated or controlled thereby ensuing wirelessly. This permits the patient support table to be located at an arbitrary position in the examination room.

Figure 4:
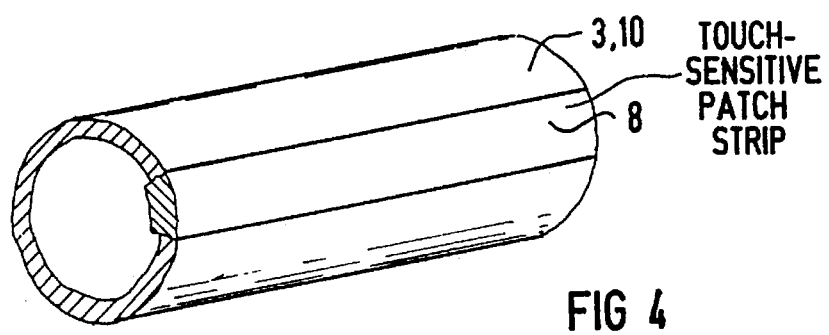
FIG. 4 shows a detail of the carrier of the operating mechanism of FIGS. 1, 2 and 3.

As shown in FIG. 4, the inner surface (i.e., the surface facing toward the patient support table) of the carrier 3 has a touch-sensitive patch strip 8 embedded therein. The patch strip 8 is connected in a circuit which includes at least one position control element 11, contained, for example, in the pedestal 2 as schematically indicated in FIG. 1. The position control element 11 may, for example, be a magnetic brake which is automatically released when the carrier 3 is gripped by an attendant, such gripping being sensed by the patch strip 8. The shape of the carrier 3 permits the support surface 1 to be adjusted in position by manipulating the carrier 3, and after the support surface 1 has been moved to a selected position, releasing one's grasp on the carrier 3 automatically causes the magnetic brake to again become engaged to hold the support surface 1 at the selected position. Since the patch strip 8 extends along the entire length of the carrier 3, a positioning control signal, such as a signal for releasing the magnetic brake, can be generated at any arbitrary location along the carrier 3. Such positioning or adjustment of the support surface 1 can be undertaken by a second attendant, while a first attendant actuates the operating elements 5, 6 and 7.

Because the operating elements 5, 6 and 7 are removable from the carrier 3, they can easily be cleaned and sterilized, or replaced as needed. Moreover, there respective positions along the length of the carrier 3 can be adjusted by either releasing the clamps which respectively hold them in place, or if the clamps are frictional clamps, the elements 5, 6 and 7 can be slid along the length of the straight section of the carrier 3.

Feed and/or control lines 9 for the operating elements 5, 6 and 7 can be contained in the carrier 3, which may be in the form of a bent tubular rod. These lines 9 can be electrically connected to the operating elements 5, 6 and 7 via releasable contacts. If, as is preferable, the operating elements 5, 6 and 7 are remote control elements, only power supply lines need be contained within the carrier 3. Moreover, each of the control elements 5, 6 and 7 may contain a battery which is charged by the lines 9 when the elements 5, 6 and 7 are mounted on the carrier 3. When removed from the carrier 3, the operating elements can then be used at any location in the examination room.

A second carrier with duplicate operating elements, corresponding to the carrier 3 and the operating elements thereon, or with different operating elements, can be disposed at the longitudinal side of the support surface 1 opposite from the side to which the carrier 3 is disposed in FIG. 1. This permits optional operation from either side of the patient table.

Another carrier 10, pivotably mounted to the support surface in the same manner as the carrier 3, can be provided on the same side of the patient support table as the carrier 3. The carrier 10 can have duplicate operating elements 5, 6 and 7 mounted thereon, or different operating elements. The position of the carrier 10 is particularly suited for conducting examinations in the region of the patient's upper body and head. A carrier corresponding to the carrier 10 can also be provided on the opposite side of the support surface 1.

In addition to enabling removability and replaceability of the operating elements 5, 6 and 7, the mounting angles of the operating elements 5, 6 and 7 on the carriers 3 and 10 can be selectively adjusted, since the carriers 3 and 10 have a round cross section. This permits the individual operating elements to be mounted at respective angles which are most comfortable for a particular attendant to manipulate. Moreover, the operating elements 5, 6 and 7 need not be duplicated on both carriers 3 and 10; one set of operating elements can be provided which can then be removed from one carrier and mounted on the other, as needed.

Although modifications and changes may be suggested by those skilled in the art, it is the intention of the inventor to embody within the patent warranted hereon all changes and modifications as reasonably and properly come within the scope of his contribution to the art.

I claim as my invention:

1. An operating mechanism for an x-ray system having a plurality of examination components, including a patient support table having a longitudinal axis, said operating mechanism comprising:

a carrier having opposite U-shaped ends each having a first leg and a second leg, and a straight section joining the respective second legs of each U-shaped end and extending substantially parallel to said longitudinal axis of said patient support table;

means for pivotably attaching each of said first legs of said U-shaped ends to one side of said patient support table for pivoting said carrier from a position beneath said patient support table which permits unimpeded access to said patient support table and a position wherein said carrier is cantilevered so as to extend from said side of said patient support table; and at least one manually actuatable element mounted on said straight section of said carrier for operating one of said components of said x-ray system.

2. An operating mechanism as claimed in claim 1 further comprising a second carrier, identical to said carrier, disposed at an opposite side of said patient support table.

3. An operating mechanism as claimed in claim 1 wherein said patient support table has a central longitudinal region and wherein said carrier is disposed at said central longitudinal region, and further comprising an additional carrier disposed at one end of said patient support table beyond said central longitudinal region.

4. An operating mechanism as claimed in claim 1 wherein said manually actuatable element comprises a manually actuatable element removably mountable on said carrier.

5. An operating mechanism as claimed in claim 1 wherein said means for pivoting comprises means for positioning said carrier at one of a plurality of latched positions.

6. An operating mechanism as claimed in claim 1 wherein said carrier is hollow, and further comprising a plurality of electrical lines contained in said carrier and electrically connected to said manually actuatable element.

7. An operating mechanism as claimed in claim 1 wherein said manually actuatable element comprises a wireless remote control manually actuatable element.

8. An operating mechanism as claimed in claim 1 wherein said patient support table has a table top and includes means for controlling a position of said table top, and wherein said carrier is mounted to said table top end wherein said operating mechanism further comprises a touch-sensitive control strip embedded in said carrier for controlling said means for positioning said table top when said carrier is grasped.

9. An operating mechanism as claimed in claim 8 wherein said carrier has an exterior circumference, and wherein said touch-sensitive control strip has an exterior surface coinciding with said exterior circumference.

\* \* \* \* \*